United States Patent [19]

Hesse

[11] Patent Number: Plant 6,221

[45] Date of Patent: Jul. 12, 1988

[54] CHRYSANTHEMUM PLANT NAMED BRONZE PARASOL

[75] Inventor: Peter S. Hesse, Bradenton, Fla.

[73] Assignee: Ball PanAm Plant Company, Parrish, Fla.

[21] Appl. No.: 873,806

[22] Filed: Jun. 12, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Bronze Parasol having combined features of flat capitulum form and daisy capitulum type, large bronze ray florets which vary in shape from flat to spoon to quilled, with the bronze color fading evenly, eight week response period, 100–140 mm diameter across the face of the capitulum, relatively large leaves, and relatively tall plant height.

1 Drawing Sheet

The present invention comprises a new and distinct cultivar of *Chrysanthemum morifolium*, Ramat., hereinafter referred to by the cultivar name Bronze Parasol.

Bronze Parasol was originated from a mutation resulting from a controlled radiation program in Parrish, Fla. in 1983. The purpose of the radiation program was to expand the color range of the parent cultivar Parasol, disclosed in a pending application of the present inventor and Leonard H. Shoesmith. Tissue cultured plants of Parasol were irradiated in the program with 900 rads of X-ray energy.

Bronze Parasol was discovered and selected as one flowering plant within the parent plants by Peter S. Hesse in March of 1983 in a controlled environment in Parrish, Fla.

The first act of asexual reproduction of Bronze Parasol was accomplished when vegetative cuttings were taken from the initial selection in August of 1983 in a controlled environment in Parrish, Fla. by a technician working under formulations established and supervised by Peter S. Hesse. Horticultural examination of selected units initiated in November of 1983 has demonstrated that the combination of characteristics as herein disclosed for Bronze Parasol are firmly fixed and are retained through successive generations of asexual reproduction.

Bronze Parasol has not been observed under all possible environmental conditions. The phenotype may vary significantly with variations in environment such as temperature, light intensity and day length. The following observations, measurements and comparisons describe plants grown in Parrish, Fla. and West Chicago, Ill. under greenhouse conditions which approximate those generally used in commercial practice.

The following traits have been repeatedly observed and are determined to be basic characteristics of Bronze Parasol, which in combination distinguish this Chrysanthemum as a new and distinct cultivar:

1. Eight week response period.
2. Flat capitulum form; novelty daisy type.
3. Rich copper bronze color which fades evenly. Under high temperatures (above 85° F. night) the color tends toward a more pale yellow.
4. Ray florets are large, up to 65 mm long and 12 mm wide. They vary in form from almost flat to spoon to almost completely quilled; the number of ray florets per flower ranges up to as many as 35.

5. The generally tan color of the quills or tubes provides a striking contrast with the copper bronze color of the ray florets.
6. Diameter across the face of the capitulum is 100–140 mm.
7. Each plant produces 3–4 breaks after pinching.
8. Leaves are large, being up to 140 mm long and 90 mm wide.
9. Plant is tall, extending above the edge of the pot about 300 mm depending on the growing conditions.

Of the many commercial cultivars known to the present inventor, the most similar in comparison to Bronze Parasol is Parasol. In comparison to Parasol, Bronze Parasol has a medium bronze flower color, totally unlike the purple ray floret color of Parasol. All other characteristics of Bronze Parasol are essentially the same as those same characteristics of Parasol.

The accompanying photographic drawing shows typical inflorescence and foliage characteristics of Dark Parasol. The drawing comprises a black and white photograph with one flower being colored to depict tube and ray floret color.

In the following description, color references are made to The Royal Horticultural Society Colour Chart. The color values were determined between Noon and 1 p.m. on May 21, 1986 under fluorescent light at Bradenton, Fla.

Classification:

*Botanical.*—*Chrysanthemum morifolium*, Ramat., cv Bronze Parasol.

*Commercial.*—Pot mum.

INFLORESCENCE

A. Capitulum:

*Form.*—Flat.

*Type.*—Single or daisy.

*Diameter across face.*—100–140 mm.

B. Corolla of ray florets:

*Color (General tonality from a distance of three meters).*—Bronze (upper surface of ray florets).

*Color.*—Tubes approximately 164D; upper surface of spoons when opening at low temperatures (58°–75° night) close to 166B, under surface ranging from 164D to 166C.

C. Corolla of disc florets:

*Color (mature).*—Yellow.

*Color (immature).*—Yellow-green.

D. Reproductive organs:

*Androecium.*—Present in disc florets only; many.

*Gynoecium.*—Present in disc and ray florets; many.

PLANT

A. General appearance:

*Height.*—30–35 cm above the edge of the pot.

B. Foliage:

*Color (upper surface).*—147A.

*Color (under surface).*—147B.

*Shape.*—Generally elliptical; margins deeply lobed and serrated.

I claim:

1. A new and distinct cultivar of Chrysanthemum plant named Bronze Parasol, as described and illustrated, and particularly characterized by the combined features of flat capitulum form and daisy capitulum type, large bronze ray florets which vary in shape from flat to spoon to quilled, with the bronze color fading evenly; eight week response period, 100–140 mm diameter across the face of the capitulum, relatively large leaves, and relatively tall plant height.

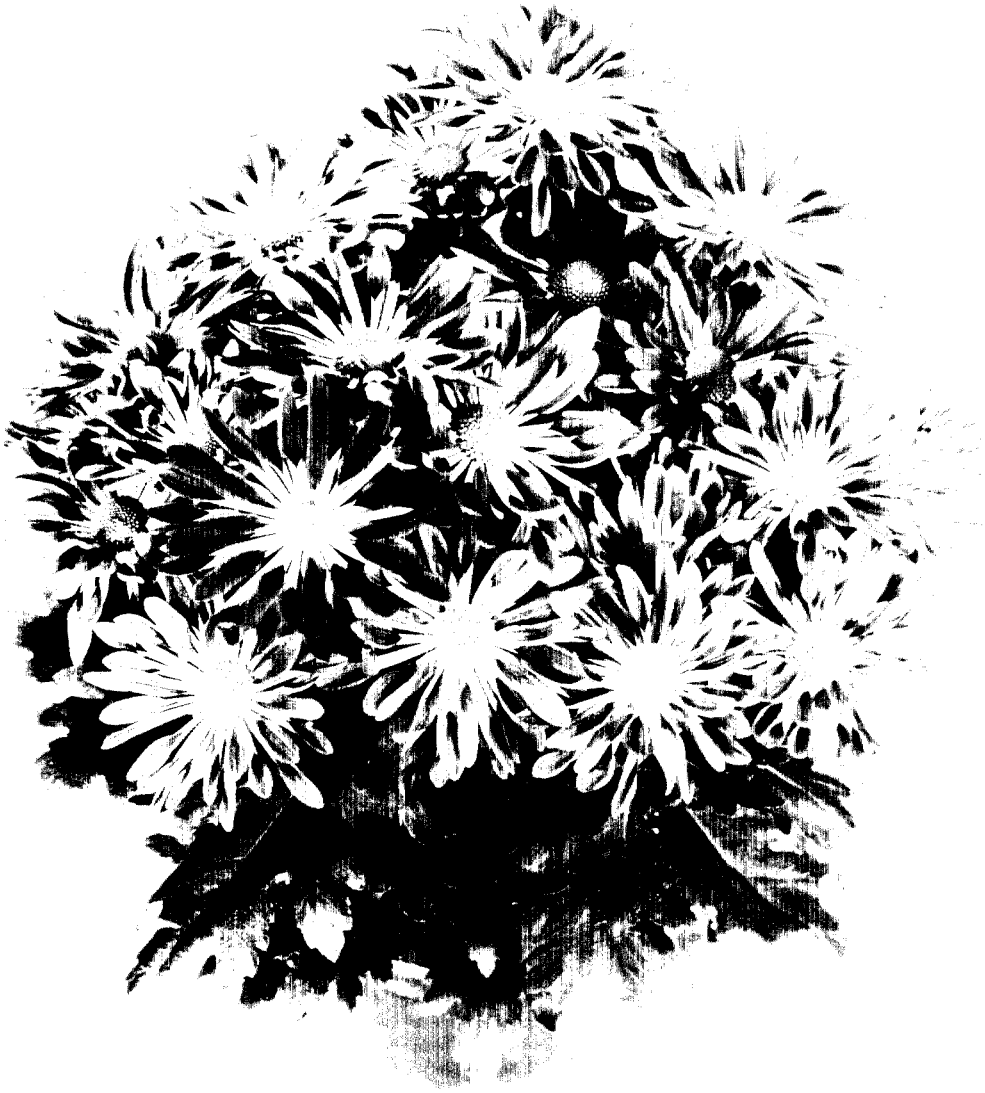

* * * * *